US010214559B2

(12) United States Patent
Modinger et al.

(10) Patent No.: US 10,214,559 B2
(45) Date of Patent: Feb. 26, 2019

(54) PROTEIN RECOVERY

(71) Applicant: Heriot-Watt University, Edinburgh (GB)

(72) Inventors: Julio Enrique Traub Modinger, Edinburgh (GB); Jane Samantha White, Edinburgh (GB); Dawn Louise Maskell, Cupar Fife (GB); Alan John Harper, Edinburgh (GB); Paul Shane Hughes, Corvallis, OR (US); Nicholas Allen Willoughby, Livingston (GB)

(73) Assignee: Heriot-Watt University, Edinburgh (GB)

(*) Notice: Subject to any disclaimer, the term of this patent is extended or adjusted under 35 U.S.C. 154(b) by 124 days.

(21) Appl. No.: 15/323,259

(22) PCT Filed: Jul. 2, 2015

(86) PCT No.: PCT/GB2015/051944
§ 371 (c)(1),
(2) Date: Dec. 30, 2016

(87) PCT Pub. No.: WO2016/001683
PCT Pub. Date: Jan. 7, 2016

(65) Prior Publication Data
US 2017/0145052 A1 May 25, 2017

(30) Foreign Application Priority Data
Jul. 3, 2014 (GB) .................................. 1411943.2

(51) Int. Cl.
*C07K 1/14* (2006.01)
*C07K 1/22* (2006.01)
*A23K 10/38* (2016.01)
*A23K 50/80* (2016.01)
*C07K 14/81* (2006.01)
*A23K 20/147* (2016.01)
*C07K 14/415* (2006.01)

(52) U.S. Cl.
CPC ............... *C07K 1/22* (2013.01); *A23K 10/38* (2016.05); *A23K 20/147* (2016.05); *A23K 50/80* (2016.05); *C07K 1/145* (2013.01); *C07K 14/415* (2013.01); *C07K 14/8121* (2013.01); *Y02A 40/818* (2018.01); *Y02P 60/873* (2015.11)

(58) Field of Classification Search
None
See application file for complete search history.

(56) References Cited

U.S. PATENT DOCUMENTS 2,446,913 A 8/1948 Erlich
3,838,143 A 9/1974 Grant
4,218,490 A 8/1980 Phillips et al.
4,359,430 A 11/1982 Heikkila et al.
5,278,284 A 1/1994 Lusk et al.
5,384,035 A 1/1995 Smolnik et al.
6,099,654 A 8/2000 Kaneko et al.

FOREIGN PATENT DOCUMENTS

| EP | 1927291 A1 | 6/2008 |
| GB | 1347933 A | 2/1974 |
| GB | 2094804 A | 9/1982 |
| IE | 980676 A1 | 11/2000 |
| JP | H06107611 A | 4/1994 |
| JP | 2005281159 A | 10/2005 |
| WO | WO-9119780 A1 | 12/1991 |
| WO | WO-2013021161 A2 | 2/2013 |

OTHER PUBLICATIONS

Bayrak, Sinasi, "International Search Report," prepared for PCT/GB2015/051944, dated Sep. 15, 2015, three pages.
Shurson, J.; "Maize Dried Distillers Grains With Solubles (DDGS)—A New Alternative Ingredient in Aquafeeds"; World Aquaculture; Sep. 2012; pp. 54-58.
Cheng, Z.J., et al.; "Effects of Microbial Phytase Supplementation in Corn Distiller's Dried Grains with Solubles on Nutrient Digestibility and Growth Performance of Rainbow Trout, *Oncorhynchus mykiss*"; Journal of Applied Aquaculture, vol. 15, No. 3; Jun. 2004; pp. 83-100.
Cheng, Z.J., et al.; "Nutritional Value of Diets Containing Distiller's Dried Grain with Solubles for Rainbow Trout, *Oncorhynchus mykiss*"; Journal of Applied Aquaculture, vol. 15, No. 3; Jun. 2004; pp. 101-113.
Leiper, K.A., et al.; "Beer Polypeptides and Silica Gel: Part II. Polypeptides Involved in Foam Formation"; Journal of the Institute of Brewing, vol. 109, No. 1; Jan. 2013; pp. 73-79.
Randall, K.M., et al.; "Fractionation of Wheat Distiller's Dried Grains and Solubles Using Sieving Increases Digestible Nutrient Content in Rainbow Trout"; Animal Feed Science and Technology, vol. 159; Aug. 2010; pp. 138-142.
Cheng, Z.J., et al.; "Effects of Supplementing Methionine Hydroxy Analogue in Soybean Meal and Distiller's Dried Grain-Based Diets on the Performance and Nutrient Retention of Rainbow Trout [*Oncorhynchus mykiss*(Walbaum)]"; Aquculture Research, vol. 34; Nov. 2003; pp. 1303-1310.

(Continued)

*Primary Examiner* — Anand U Desai
(74) *Attorney, Agent, or Firm* — Winstead PC

(57) ABSTRACT

There is provided a process for producing proteins from the by-product streams arising from distillation processes, in particular the by-product stream known as "pot ale" or "burnt ale" and the use of such proteins as protein feed ingredients or food additives.

11 Claims, 6 Drawing Sheets
Specification includes a Sequence Listing.

(56) References Cited

OTHER PUBLICATIONS

Stone, David A.J., et al.; "Effects of Extrusion on Nutritional Value of Diets Containing Corn Gluten Meal and Corn Distiller's Dried Grain for Rainbow Trout, Oncorhynchus mykiss"; Journal of Applied Aquaculture, vol. 17, No. 3; Sep. 2008; 20 pages.

Reveco, F.E., et al.; "Aqueous Fractionation Improves the Nutritional Value of Wheat Distillers Grains for Rainbow Trout (*Oncorhynchus mykiss*)"; Aquaculture Nutrition, vol. 18; Jul. 2011; pp. 202-210.

Traub, Julio, et al.; "Whiskey Co-Products, a sustainable protein source for Aquaculture feeds," Aquaculture Europe 2013—Trondheim, Norway; Aug. 11, 2013; 3 pages.

Palmer, Roxanne; "Whiskey Salmon: Scottish Scientists Find Way to Feed Fish with Distillery Byproduct," International Business Times; Oct. 4, 2013; 2 pages.

PROTEIN RECOVERY

FIELD OF THE INVENTION

This invention relates to a process for producing proteins from the by-product, co-product and waste streams arising from distillation processes. The process of the invention recovers, in a high yield, proteins, peptides and/or amino-acids contained within yeast or other cell types, as well as proteins, peptides and/or amino-acids extracted from grains or cereals to provide a substantially metal free, high purity, protein or protein rich food additive which provides advantageous amino acid ratios. In particular, the process of the invention involves treating the by-product stream known as "pot ale" or "burnt ale".

BACKGROUND OF THE INVENTION

Using the manufacture of ethanol for its use in Scotch malt whisky as an example, crushed malted barley grain is used as a carbohydrate source and this is mixed with hot water to solubilise sugars present in the barley. For malt whisky, no grain other than malted barley is used. The lignocellulosic solid matter provided by such a process is separated to leave a sugar rich liquor known as "wort". The wort can contain up to 20% protein in dry matter. The separated lignocellulosic solid matter (mainly malted grain known as "draft") can be dried, or mixed with other additives for use as a versatile animal feed stock for cattle, sheep, pigs and horses.

In a typical distillation process, the wort is transferred to a large vessel(s) known as 'washbacks' and fermented by adding yeast. The yeast converts the sugar in the wort to ethanol, creating what is known as the 'wash' and the fermentation is allowed to proceed until the desired alcohol content, typically around 8%, is reached. At the end of the fermentation process, the fermented wash is charged to a first distillation vessel (the wash still). In traditional Scotch malt whisky manufacture, the distillation vessels or stills are made of copper (Cu) metal whereas for grain whisky, sacrificial copper components may be used. Copper is commonly used due to its ability to be easily shaped into intricate designs and its rate of heat transfer. The stills are heated to drive off the ethanol and the ethanol is then condensed to a liquid. This distillate is then charged to a second distillation vessel (the spirit still). In the spirit still, the ethanol is re-distilled to increase its purity before it is cooled and recovered as a liquid for maturation in oak casks. By law, it cannot be Scotch whisky until it has matured in oak casks in Scotland for at least three years.

Once the first distillation is complete, the liquid residue that remains in the wash still after distillation is known as "pot ale" or less commonly "burnt ale". Pot ale is a low pH liquid that contains dead yeast cells, yeast residues, carbohydrates, protein material from the yeast, microbes (*Lactobacillus* species) and the grain residues and extracts.

Whilst the pot ale by-product generated may be rich in nutrients it typically has a high chemical or biological oxygen demand (COD or BOD) making the pot ale by-product difficult to process and dispose.

Further, during brewing and distilling, a small amount of copper metal of the still typically transfers to the pot ale through abrasion or dissolution where it remains in solution or bound to suitable ligands. Whilst copper is an essential trace element for life, it is well understood that copper (and other materials) are bio-accumulative in the livers of certain mammals (e.g. sheep and goats) and that this bio-accumulation can reach acute/toxic levels.

With a low solids content, pot ale may be concentrated using evaporation or other means for use as an animal feed additive known as "pot ale syrup". Evaporation is an energy intensive method which suffers from high cost. Additionally evaporation can suffer from high greenhouse gas emissions and the high temperatures used may have a deleterious effect on protein quality. Evaporation concentrates all the components in pot ale, including non desirable compounds such as phytate and copper. Typically, the pot ale syrup is mixed with the recovered draff and dried to make animal feed known as distillers' dark grains. However, in view of the presence of copper the use of pot ale syrup and distillers' dark grains as feeds is restricted to cattle, horses and pigs. Examples of the use of pot ales as a feed additive and pot ale processing methods are described in GB2094084 (Gilmour et al), EP1927291 (Atherton et al) and IE980676 (Court et al).

Pot ale by-products generated from grain fermentation may contain at least 20% protein as dry matter. It has been realised that this protein has a commercial value as a feed additive and efforts to recover this protein by precipitation or flocculation at a high pH have been employed. In the process described in GB2094084, the pot ale is treated with a caustic material (NaOH, KOH or Ammonium Hydroxide) to raise the pH to greater than neutral pH causing flocculation of the protein. The protein is then allowed to settle before mechanical recovery. This requires a large volume of caustic material, can be expensive and furthermore, not all protein is recovered using this process, since only proteins with iso-electric pH lower than neutral pH will precipitate, whereas those above neutral pH will still remain in solution. A protein recovery of 50-60% is typical.

In GB1347933 (NESTLE) a multistep process is discussed wherein an alkaline protein solution is filtered through a macro-reticular ion exchange resin before removing the alkali (Ammonia, NH3) through heat treatment to give purified protein. A disadvantage of this process is that it is limited to alkaline pH starting material.

It would be advantageous if by-products arising from distillation processes could be tailored for specific animal and fish feed applications.

Whilst distillery by-products have been used in aquaculture (Randall and Drew, 2010 [Randall, K. M., Drew, M. D., 2010. Fractionation of wheat distiller's dried grains and solubles using sieving increases digestible nutrient content in rainbow trout. Anim. Feed Sci. Technol. 159, 138-142]; Shurson 2012 [Shurson, J., 2012. Maize dried distillers grains with solubles (DDGS)—a new alternative ingredient in aquafeeds. World Aquaculture. September 2012. pp. 54-58]), their use is restricted by the high fibre content (at the expense of protein) and also the presence of phytate with supplementation with essential amino acids such as lysine and methionine or phytase required to achieve higher incorporation levels in the total fish feed (Reveco et al., 2012 [Reveco, F. E., Collins, S. A., Randall, K. M., Drew, M. D., 2012. Aqueous fractionation improves the nutritional value of wheat distillers dried grains for rainbow trout (*Oncorhynchus mykiss*). Aquacult. Nutr. 18, 202-210.]; Stone et al., 2005 [Stone, D. A. J., Hardy, R. W., Barrows, F. T., Cheng, Z. J., 2005. Effects of extrusion on nutritional value of diets containing corn gluten meal and corn distiller's dried grain for rainbow trout, *Oncorhynchus mykiss*. Journal of Applied Aquaculture 17:1-20]; Cheng et al., 2003 [Cheng, Z. J., Hardy, R. W., Blair, M., 2003. Effects of supplementing methionine hydroxyl analogue in soybean meal and distiller's dried grain-based diets on the performance and nutrient retention of rainbow trout [*Oncorhynchus mykiss* (Walbaum)]. Aquaculture Research 34:1303-1310.]; Cheng and Hardy 2004a [Cheng, Z. J., Hardy, R. W., 2004a. Effects of microbial phytase supplementation in corn distiller's dried grains with solubles on nutrient digestibility and growth performance of rainbow trout (*Oncorhynchus mykiss*). Journal of Applied Aquaculture 15:83-100.]; Cheng and Hardy 2004b [Cheng, Z. J., Hardy, R. W., 2004b. Nutritional value of diets containing distiller's dried grain with solubles for rainbow trout (*Oncorhynchus mykiss*). Journal of Applied Aquaculture 15:101-113.]).

SUMMARY OF THE INVENTION

The inventors have determined a process that concentrates the protein provided in by-products of distillation, while removing and minimising compounds such as Cu, fibre, phytate, polyphenols and carbohydrates, which currently restricts the use of pot ale syrup as a feed to cattle, horses and pigs. Further the process can be used to selectively separate specific proteins or a mixture of proteins from by-products of distillation allowing further value to be realised from, for example pot ale.

In particular, the present inventors have determined a process of treating a by-product stream, suitably "pot ale" or "burnt ale" from distillation processes that contain yeast cells and/or cereal proteins to provide a high protein/high proteinaceous matter source. This source can be used for example, for use in aquaculture. In particular the process can be useful to provide a composition with a protein content in excess of 50% with low levels of copper, phytate, fibre and polyphenols. Low copper levels, at less than 10 mg/kg feedingstuff, are preferred if the composition is to be used for feeding to sheep. Similarly, control of fibre levels and reduced levels of phytate and polyphenols are critically important for pet food applications. In embodiments, the process can utilise a lysing agent or a lysing process to increase the measured Nitrogen (protein) content of the by-product or waste, to provide recovery, in a high yield, a high purity metal free proteinaceous material/protein. The process can utilise a regenerative adsorption matrix either as a slurry or packed into a column or similar vessel wherein the by-product stream is contacted with either the packed matrix or the slurry to allow the protein or proteinaceous material in the by-product to be bound by the packed matrix or slurry matrix. The proteinaceous matter/protein is then recovered in a solution phase through a selective binding and desorption/elution from the packed solid matrix or matrix forming the slurry. The regenerative adsorption matrix can encompass an ion exchange support matrix, including anionic or cationic adsorbents. In embodiments such an adsorption matrix can have a high silica content (for example, a silica content of greater than 50, 55, 60, 65, 70, 75, 80, 85, 90, 95 or 100% wt) and include diatomaceous earth, kieselguhrs, bentonites or zeolites which can bind to the proteinaceous component of the by-product stream arising form a distillation process. The binding of the adsorption matrix can be influenced by altering the charge present on the surface of the adsorbent by for example altering the salt concentration or pH at the surface of the adsorption matrix. In embodiments the proteinaceous component of the by-product stream, for example pot ale can bind to the adsorption matrix without requiring any change of pH of the by-product stream.

By using a regenerative adsorption matrix, the process of the invention is low cost and further provides a protein depleted waste stream that can be easily disposed. This stream, with reduced nitrogen levels, is particularly suited to anaerobic digestion. The streams resulting from equilibration and regeneration of the adsorption matrix are also suitable for the anaerobic digestion process and can be used as conditioners in the system.

Additionally, the recovered proteinaceous/protein matter is substantially free from metal ions such as copper (Cu) thus rendering, for example, a pot ale by-product, suitable for use as high value, protein rich, animal feed additive. This feed additive can be suitable for animal species that bio-accumulate copper or other metals to potentially toxic levels.

According to a first aspect of the invention, there is provided a process for the recovery of proteinaceous matter, from a by-product stream arising from distillation processes, the process comprising the steps:

optionally, lysing or disrupting cells present in the by-product stream;

removing insoluble solid matter from the by-product stream to yield a clarified proteinaceous matter containing solution;

contacting the clarified proteinaceous matter containing solution with an adsorption matrix under conditions such that the proteinaceous matter binds to the adsorption matrix wherein the adsorption matrix comprises a silica content of greater than 50% wt; and altering the conditions to cause release of all of or a specific fraction of the proteinaceous matter bound to the adsorption matrix.

Suitably, proteinaceous matter may comprise any one of protein, peptide, amino acids or combinations thereof. Suitably the steps of contacting the proteinaceous matter containing solution with an adsorption matrix, is performed without prior purification steps being performed, suitably on the clarified proteinaceous matter containing solution formed from removal of solid matter from the by-product stream without further pre-treatment of the solution, for example without any changes in pH of the by-product stream, in particular pot ale. The adsorption matrix can act as an ion exchange media which provides for a reversible interaction between a charged protein and an oppositely charged matrix. The adsorption matrix can be an anion or cation exchanger. In embodiments, the binding of the proteins of the by-product, in particular pot ale, prior to any pH adjustment of the by-product (about pH 3 to 4) is indicative that the high silica content adsorbent matrix can act as a cationic ion exchanger and that separation is based on ion exchange. Molecular sieving and electrostatic interactions may also be involved.

In embodiments the step of removing insoluble solid matter from the by-product stream can utilise a two stage process. Suitably, the first stage can remove solids of a size greater or equal to 5 µm. In embodiments a first stage can use disc stack centrifuges, scroll decanters or hydroclones. In embodiments the first stage can exert a centrifugal force of at least 4000 g. In embodiments a second solid removal stage may remove solids between 0.1-5 µm, in embodiments 0.1-1 µm. Suitably, the second solid removal stage may utilise filter bags or filter cartridges. In embodiments the second stage can utilise filters of less than or equal to 5 µm, in embodiments less than or equal to 1 µm. In embodiments the insoluble solids from stage 1 and/or stage 2 can be dried and/or concentrated. In embodiments, the clarified protein containing solution can be concentrated prior to the contacting step.

Optionally the process can further include the step of regenerating the adsorption matrix.

The inventors have determined that utilising the process as taught herein, proteinaceous matter including specific protein products with properties (such as advantageous amino acid ratios or proteins with advantageous functions) that allow the protein products to be used as nutritional additives and/or as functional ingredients in formulations for human, animal, pet and fish foodstuffs can be provided.

Whilst advantageously the process of the invention is directed towards treatment of distillery by-product streams such as pot or burnt ale, other waste cellular material, for example media or suspensions containing live or dead cell cultures could be treated in a similar manner to recover the protein. In embodiments the by-product or waste stream to be treated may be derived from the distillation of an alcohol. In embodiments the by-product or waste stream can contain yeast cells.

In embodiments the by-product stream can be selected from pot ale, spent wash, spent lees, stillage, draff, spent grain, hot (trub) or cold break or from any other residue or by-product from an alcohol or biofuel distillation process or combinations of such by-product streams.

In particular, the examples of the present invention are focused on the preparation of a protein product from pot ale. Pot ale is the liquid residue that remains in the wash still after distillation. It is also less commonly known as "burnt ale". Pot ale is a low pH liquid that contains dead yeast cells, yeast residues, carbohydrates, protein material from the yeast, bacteria and the grain residues and extracts. It contains at least 1% suspended solids (mainly yeast cells), 4% dissolved solids, and approximately 30% crude protein content on a dry matter basis. The typical protein content of pot ale as distributed between the dissolved solids and suspended solids fraction is provided in Example 1.

In particular embodiments the process provides for the recovery of protein material from cellular suspensions such as pot or burnt ale wastes from distilling processes such that the recovered protein material is substantially reduced in polyphenol, phytate, metal, minerals and carbohydrate.

Suitably the by-product stream may have a pH range of between 2 to 6. In embodiments, where the pH of a by-product stream, for example pot ale, has a low pH (a pH range of between 2 to 6) this can lead to most of the proteins present therein carrying a positive charge. In embodiments a cation exchange resin can be used as the adsorption matrix.

The inventors have found that particular adsorption matrices are advantageous to bind both proteins from grains, as well as yeast protein from a by-product stream, for example pot ale, in a single step, without requiring a change in the acidic pH of pot ale. Using this process, it has been determined a protein recovery yield in excess of 70% in particular in excess of 75%, 85%, 90% or 95% can be obtained from pot ale waste derived from an alcohol distillation.

An adsorption matrix, suitable for use to bind protein in the by-product stream may be and ion-exchange matrix which is cationic or anionic in nature and can be selected based on its cost or other desired chemical or physical property; advantageously the media includes an ionic group or groups that provide(s) sites to temporarily bind protein molecules. Advantageously the adsorption matrix can be selected such that it provides low compressibility to allow flow of material through the media without high pressure drops.

A high silica content adsorption matrix is provided. A high silica content adsorption matrix may have a silica content of greater than 50, 55, 60, 65, 70, 75, 80, 85, 90, 95 or 100% wt.

A commercially available adsorbent with a high silica content may be used.

The silica may be a natural silica or a synthetic silica.

The adsorption matrix may be an aluminosilicate matrix. The adsorption matrix may have an aluminosilicate content of greater than 50, 55, 60, 65, 70, 75, 80, 85, 90, 95 or 100% wt.

The adsorption matrix may comprise a clay mineral. For example, a natural clay mineral. Clay minerals are composed of silica, alumina or magnesia or both, and water. Clay minerals may comprise hydrous aluminium phyllosillicates. One example of a clay mineral that can be used is bentonite. The adsorption matrix may have a clay mineral content of greater than 5, 10, 15, 20, 25, 30, 35, 40, 45, 50, 55, 60, 65, 70, 75, 80, 85, 90, 95 or 100% wt.

The adsorption matrix may comprise zeolite. In its broadest sense, zeolites can be termed day minerals. Zeolites are crystalline aluminosilica compounds. The zeolite may be a natural zeolite or a synthetic zeolite. Suitably a zeolite clinoptilolites can be used. One example of a zeolite that can be used is "zeolite C". The adsorption matrix may have a zeolite content of greater than 5, 10, 15, 20, 25, 30, 35, 40, 45, 50, 55, 60, 65, 70, 75, 80, 85, 90, 95 or 100% wt.

The adsorption matrix may comprise diatomaceous earth or kieselguhrs. The adsorption matrix may have a diatomaceous earth or kieselguhrs content of greater than 5, 10, 15, 20, 25, 30, 35, 40, 45, 50, 55, 60, 65, 70, 75, 80, 85, 90, 95 or 100% wt.

These high silica content adsorption matrices have been determined by the inventors to bind to proteins in pot ale at the low pH range at which it is produced in distilleries. This allows the selective separation of the proteins from components in pot ale such as polyphenols, phosphorous, phytate and elements including Cu. It has not been previously recognised that the proteins in pot ale can be readily separated from the other pot ale components using such high silica content adsorbent matrices and that the proteins can be bound to such matrices without prior pH adjustment of the pot ale. This provides a simple process to remove the proteins and then to selectively desorb them from the matrix. It also allows control of the profile of the protein mixture. It is also surprising that these proteins, once recovered from the matrix, maintain functional properties such as foaming ability.

The adsorption matrix may comprise a combination of any one of the following: one or more clay minerals, zeolites and/or diatomaceous earth or kieselguhrs.

In embodiments, particle sizes of adsorbents greater than 35 micrometers, preferably greater than 40 micrometers may be used. For example, particle sizes from 40 micrometers to 700 micrometers may be used. Ranges of particle size may also be used. For example, a particle size range of 300-700 micrometers may be used.

Particle size can be restricted by sieving the particles to positively select or negatively select the particle size(s) desired. Prior to the step of contacting the protein containing solution with the adsorption matrix, the particles for use as the adsorbent may be classified, packed into a bed and equilibrated in a chromatographic column.

In embodiments the adsorption matrix may be a strong cation exchange material or column.

In embodiments commercially available absorbents with high silica content (>70%) can be used as the adsorption or ion exchange matrices, for example diatomaceous earth, bentonites, kieselguhrs, and/or zeolites. Suitably a zeolite, in particular zeolite clinoptilolite, also known as "zeolite C" can be used.

In embodiments, the adsorption matrix can be formed from zeolites (crystalline aluminosilica compounds), in particular clinoptilolites. These have been determined by the inventors to bind to proteins in pot ale at the low pH range at which it is produced in distilleries. This allows the selective separation of the proteins from components in pot ale such as polyphenols, phosphorous, phytate and elements including Cu. It has not been previously recognised that the proteins in pot ale can be readily separated from the other pot ale components using natural clay minerals and that the proteins can be bound to the matrix without prior pH adjustment of the pot ale. This provides a simple process to remove the proteins and then to selectively desorb them from the matrix. It also allows control of the profile of the protein mixture. It is also surprising that these proteins, once recovered from the matrix, maintain functional properties such as foaming ability.

Distillation is quite a severe process and a high degree of protein denaturation and/or precipitation would be expected. For example, the first distillation step in malt whisky production typically involves maintaining the wash at temperatures between 90-100° C. until the alcohol has been evaporated. It is important to highlight that the whisky process has a number of differences compared to brewing so it is not obvious that similar proteins would be present in the by-product or product streams in distillation and whether these proteins maintain functional properties in the pot ale after distillation. During the brewing process the wort i.e. the sugar-rich extract from the malted barley, is boiled before fermentation. Hops are also included in this step and this boiling results in precipitation of proteins in addition to polyphenols as hot trub or cold break and also inactivates the proteolytic barley proteins. This step is also associated with modification of the remaining soluble proteins by glycation, acylation and denaturation reactions, which are thought to be essential in creating the foam-forming potential of proteins in the final beer. In production of distilled spirits, the wort is not boiled and the proteolytic enzymes from the malted barley are still active during fermentation with continuous proteolysis and alteration of the soluble proteins. During the first distillation step the wash i.e. the fermented liquor, is heated between 90-100° C. until the alcohol has been distilled. This is quite a severe treatment and it is surprising that the mixture of proteins remaining in the wash still after distillation are still foam-active. This activity is also maintained after the chromatography steps in the process described herein.

Whilst silica-based gels have been used to selectively bind hordein protein fragments in beer, other proteins such as LTP1 and proteins Z remained unbound (Leiper 2003 [Leiper, K. A., Stewart, G. G., McKeown, I. P. 2003. Beer polypeptides and silica gel. Part II. Polypeptides involved in form formation. Journal of the Institute of Brewing. 109: 73-79.]). It is therefore unexpected that a silica-type matrix such as zeolite can bind nearly all the proteins in pot ale and separate them from distillation by-products, especially without any prior treatment of the pot ale.

The use of high silica content matrices comprising for example zeolites offer a number of advantages over other resins such as being relatively inexpensive, food grade and having desirable physical properties such as porosity and incompressibility at the pressures required for large scale chromatographic processes. Most importantly, its inherent properties shows high affinity for the proteinaceous matter/mixture of proteins in pot ale and this allows adsorption of pot ale proteins at a pH range that doesn't require any pH change or chemical addition to the pot ale prior to protein binding to the matrix.

The conditions of the adsorption and desorption process (e.g. pH, ionic species & concentration) can be altered to selectively remove specific pot ale components such as polyphenol, carbohydrate, phytate and elements including copper ions, recover either all of the protein, part of the protein or specific protein fractions.

In embodiments, the conditions to enhance binding of the proteinaceous matter to the adsorption matrix (which can be considered as an ion exchange media) can comprise treating the matrix prior to chromatography with alkaline, acidic or neutral pH solutions or buffers such as sodium hydroxide, sodium phosphate buffer, citrate buffer or acetate buffer with a pH in the range of pH 1 to pH 12 and a salt concentration in the range 0.01 M to 2 M. In embodiments, the conditions to allow release of the proteinaceous matter/protein from the adsorption matrix (which can be considered to be an ion exchange media) can comprise a salt, for example NaCl, in the concentration range 0.5M to 2M, suitably 1M. Other alkaline, acidic or neutral pH solutions or buffers can also be used and these can comprise a phosphate or carbonate buffer in the pH range of 7-11 or 8-11 or NaOH in the concentration range 0.01 M-1.0 M or NaOH in the pH range 10-14.

In embodiments, the step of lysing the cells can comprise an enzymatic treatment. Alternatively, the step of lysing or disrupting the cells present in the by-product stream can be acid/alkaline hydrolysis, heating, osmotic pressure effects, use of solvents, surfactant treatment, sonication, rapid depressurisation or attrition, high shear processing, or combinations of these lysis or disruption steps. The method of lysis or disruption used will typically depend on the volume of material to be processed. Suitably, glucanase or protease may be provided to aid proteinaceous matter/protein release. In embodiments, the treated by-product stream can be provided at a temperature to optimise enzymatic activity. In embodiments the treated by-product stream can be provided at a pH to optimise enzymatic activity. In embodiments, the process can be undertaken in the temperature range from ambient to 90° C., preferably about 45° C.

In embodiments, 50% to 95% of the total proteinaceous matter present in the by-product stream, for example pot ale can be recovered using the process of the present invention.

In embodiments, the proteinaceous matter/soluble protein recovered from the adsorption matrix can be further processed and concentrated using an evaporator, spray drying and/or filtration methods.

The process may further include an additional chromatography step before and/or after the adsorption step, including size exclusion, affinity or other suitable chromatography steps.

In embodiments of the process, pot ale either treated or not treated to enhance release of proteinaceous matter/protein and/or to promote lysis or disruption of the cells therein can be clarified to separate the solid and liquid portions. The liquid portion can be provided to an adsorption matrix under conditions wherein the proteinaceous matter/protein of the liquid portion binds to the matrix and the resulting non-protein or low-protein liquid stream (a protein stream containing less than 50% of the original protein suitably less than 10%, less than 20% of the original protein) is separated from the proteinaceous matter/protein bound media. The conditions surrounding the adsorption matrix can then be changed such that the proteinaceous matter/protein bound to the matrix is released from the matrix and can be collected. Optionally the adsorption matrix can then be regenerated to allow further binding of proteinaceous matter/protein to the adsorption matrix. If desired, the non-protein or low-protein liquid stream created following removal of protein from the liquid portion of the clarified pot ale can be provided to the adsorption matrix, for example the regenerated adsorption matrix, for a second or further period under similar conditions to the first chromatography step.

In embodiments the adsorption matrix can be provided in a chromatography column. In embodiments, multiple chromatography columns can be run in parallel to improve throughput or in series to improve yield or purity. In embodiments the invention can be operated in a continuous, semi-continuous or discontinuous manner.

In embodiments the protein eluted from the adsorption matrix can be concentrated by ultrafiltration, diafiltration or evaporation.

In embodiments, the non-protein or low-protein liquid stream created following removal of protein from the liquid portion of the clarified pot ale can be provided to an additional treatment process such as anaerobic digestion. This stream, with reduced nitrogen levels, is particularly suited to anaerobic digestion. The streams resulting from equilibration and regeneration of the adsorption matrix are also suitable for the anaerobic digestion process and can be used as conditioners in the anaerobic system.

According to a second aspect of the present invention there is provided a proteinaceous matter, in particular proteins, in particular functionally active proteins obtained from a process of the first aspect of the invention.

The proteinaceous matter, for example proteins and/or functionally active proteins recovered by elution from the adsorption matrix and either concentrated by filtration, diafiltration or evaporation or processed without further concentration, can then be dried on its own or, dried in combination with the insoluble solids stream using a drying process or the mixed with other media such as the cereals recovered from the draft or solids from stillage or spent wash to improve the protein content of the cereals and solids without increasing the total metal content of the mixture.

In embodiments the proteinaceous matter can provide proteins from the protein Z family of barley proteins such as Serpin-Z4 (Z4) or Serpin-Z7 (Z7) or LTP1 protein. These proteins have amino acid sequences as follows (from the Swiss-Prot database, www.uniprot.org):

```
Protein Z4 (Swiss-Prot accession numer P06293):
                                                          (SEQ ID NO: 1)
         10         20         30         40         50         60
MATTLATDVR LSIAHQTRFA LRLRSAISSN PERAAGNVAF SPLSLHVALS LITAGAAATR 70         80         90        100        110        120
DQLVAILGDG GAGDAKELNA LAEQVVQFVL ANESSTGGPR IAFANGIFVD ASLSLKPSFE 130        140        150        160        170        180
ELAVCQYKAK TQSVDFQHKT LEAVGQVNSW VEQVTTGLIK QILPPGSVDN TTKLILGNAL 190        200        210        220        230        240
YFKGAWDQKF DESNTKCDSF HLLDGSSIQT QFMSSTKKQY ISSSDNLKVL KLPYAKGHDK 250        260        270        280        290        300
RQFSMYILLP GAQDGLWSLA KRLSTEPEFI ENHIPKQTVE VGRFQLPKFK ISYQFEASSL 310        320        330        340        350        360
LRALGLQLPF SEEADLSEMV DSSQGLEISH VFHKSFVEVN EEGTEAGAAT VAMGVAMSMP 370        380        390
LKVDLVDFVA NHPFLFLIRE DIAGVVVFVG HVTNPLISA Protein Z7 (Swiss-Prot accession number Q43492):
                                                          (SEQ ID NO: 2)
         10         20         30         40         50         60
MATTLTTDLR LSIAHQTRFG LRLASAISSD PESAATNVAF SPVSLHVALS LVAAGARGAT 70         80         90        100        110        120
RDQLVAVLGG GGAGEAEALQ SLAEQVVQFV LADASINSGP RIAFANGVFV DASLSLKPSF 130        140        150        160        170        180
QELAVCNYKS EVQSVDFKTK APEAASQVNS WVKNVTAGLI EEILPAGSID NTTRLVLGNA 190        200        210        220        230        240
LYFKGLWTKK FDESKTKYDD FHLLNGSTVQ TPFMSSTNKQ YLSSSDGLKV LKLPYQHGGD 250        260        270        280        290        300
NRQFSMYILL PEAHDGLSRL AQKLSTEPDF LENRIPTEEV EVGQFMLPKF KISFGFEANK 310        320        330        340        350        360
LLKTLGLQLP FSLEANLSEM VNSPMGLYIS SVFHKTFVEV DEEGTKAGAA TGDVIVDRSL 370        380        390
PIRMDFVANH PFLFLIREDI AGVVLFIGHV ANPAVSS LTP1 (Swiss-Prot accession number P07597
                                                          (SEQ ID NO: 3)
         10         20         30         40         50         60
MARAQVLLMA AALVLMLTAA PRAAVALNCG QVDSKMKPCL TYVQGGPGPS GECCNGVRDL 70         80         90        100        110
HNQAQSSGDR QTVCNCLKGI ARGIHNLNLN NAASIPSKCN VNVPYTISPD IDCSRIY
```

In embodiments the proteinaceous matter can comprise amino acid residues in the ratios.

TABLE 1

| Amino acid | % CP |
|---|---|
| Alanine | 1.8.-3.6 |
| Arginine | 2.5-6 |
| Aspartic acid | 5.8-7.4 |
| Glutamic acid | 5.2-16.08 |
| Glycine | 3.5-5.2 |
| Histidine | 0.9-6.7 |
| Isoleucine | 1.6-3.2 |
| Leucine | 1.8-5.0 |
| Lysine | 1.6-6.6 |
| Methionine | 0.3-1.9 |
| Phenylalanine | 0.8-4.0 |
| Proline | 2.4-7.7 |
| Serine | 2.8-4.2 |
| Threonine | 2.4-3.7 |
| Tryptophan | 0.3-7.2 |
| Tyrosine | 2.0-3.2 |
| Valine | 2.7-4.2 |

In particular embodiments the proteinaceous matter can comprise amino acid residues in the ratios (expressed as % crude protein)

TABLE 2

| Amino acid | % CP |
|---|---|
| Alanine | 2.3-3.1 |
| Arginine | 3.1-5.5 |
| Aspartic acid | 6.3-6.9 |
| Glutamic acid | 5.7-16.3 |
| Glycine | 4.0-4.7 |
| Histidine | 1.4-6.2 |
| Isoleucine | 2.1-2.7 |
| Leucine | 3.3-4.5 |
| Lysine | 2.1-6.1 |
| Methionine | 0.8-1.4 |
| Phenylalanine | 1.3-2.5 |
| Proline | 2.9-7.2 |
| Serine | 3.3-3.7 |
| Threonine | 2.9-3.2 |
| Tryptophan | 0.8-6.7 |
| Tyrosine | 2.5-2.7 |
| Valine | 3.2-3.7 |

According to a third aspect of the present invention there is provided an animal feed, fish feed or food ingredient comprising a proteinaceous matter, for example proteins, as set out by the first or second aspect.

According to a fourth aspect of the present invention there is provided the use of proteinaceous matter as set out by the first or second aspect as a foaming agent.

According to a fifth aspect of the present invention there is provided the use of an adsorption matrix comprising a silica content of greater than 50% wt to separate and isolate proteinaceous matter from a pot ale by-product stream from a distillation process.

Each document, reference, patent application or patent cited in this text is expressly incorporated herein in their entirety by reference, which means it should be read and considered by the reader as part of this text. That the document, reference, patent application or patent cited in the text is not repeated in this text is merely for reasons of conciseness.

Reference to cited material or information contained in the text should not be understood as a concession that the material or information was part of the common general knowledge or was known in any country.

Throughout the specification, unless the context demands otherwise, the terms 'comprise' or 'include', or variations such as 'comprises' or 'comprising', 'includes' or 'including' will be understood to imply the includes of a stated integer or group of integers, but not the exclusion of any other integer or group of integers.

Preferred features and embodiments of each aspect of the invention are as for each of the other aspects mutatis mutandis unless context demands otherwise.

SPECIFIC DESCRIPTION OF THE FIGURES

Embodiments of the present invention will now be described by way of example only, with reference to the accompany figures in which;

FIG. 1 is a schematic drawing of the process for preparing a protein product according to the invention. Stage 1 refers to solid/liquid separation and can include disk stack centrifuges, scroll decanters or hydrocylones. Stage 2 is the secondary solid removal step and comprises filter bags or filter cartridges. Stage 3 is an optional step involving drying of the solids recovered during Stage 1 and Stage 2 when a dry product rather than a slurry is required. Stage 4 is the chromatography step which allows separation of the protein mixture and may include an additional chromatography step (Stage 5) if required. Stage 6 is an ultrafiltration/diafiltration or evaporation step and Stage 7 is a further drying step which may include: cross-circulation and through-circulation driers, tray driers, tunnel driers, rotary driers, drum driers, spray driers and/or freeze drier. The drying stages (3 and 7) can be combined to provide a high-protein yeast dry product consisting of the solids removed during steps 1 and 2 and the proteins separated by chromatography. The protein depleted waste stream and the streams resulting from equilibration and regeneration of the adsorption matrix during Stage 4-5 and waste streams from Stage 6 can enter waste water treatment systems (8). These streams are particularly suited to anaerobic digestion systems and the energy generated from the anaerobic gas can be used to power other steps in the process, delivery a truly integrated process.

FIG. 2 is a flow diagram of how the matrix is conditioned for the chromatography step in Stage 4.

FIG. 3 is an image of an SDS-PAGE gel of proteins in the dissolved solids fraction of pot ale. The samples loaded in the lanes labelled 1-3 are as follows: 1. Protein standards; 2 and 3 dissolved solids fraction of pot ale (16 μg protein).

FIG. 4 is an image of an SDS-PAGE gel of pot ale proteins separated by chromatography using the Capto S column as described in Example 2. The samples loaded in lanes labelled 1-8 were eluted sequentially from the Capto S column with sodium acetate buffer containing 0.2 M NaCl (lanes 1 and 2), 0.4 M NaCl (lanes 3 and 4) and 0.6 M NaCl lanes 5 and 6. Lane 7 contains a buffer and blank lane 8 the protein standards. The protein loaded per well varied between 2-6 μg protein.

SPECIFIC DESCRIPTION OF THE INVENTION

Figure 1:
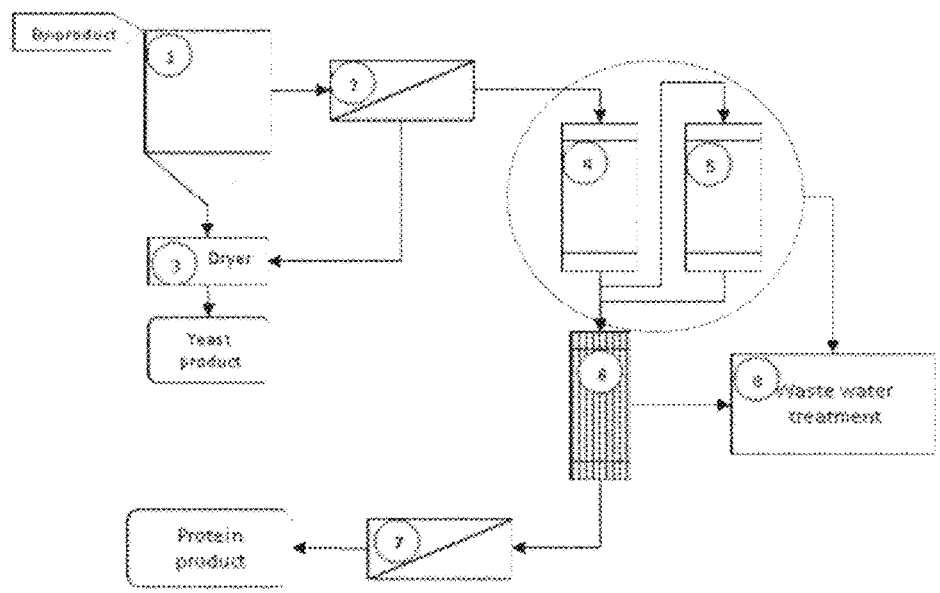

Pot or burnt ale is a high volume low solids water based stream or by product in the distilling industry that is typically acidic (low pH) and contains a high portion of protein (measured as total Nitrogen content using a Kjeldahl analysis) that is derived from brewers yeast and the fermentation media (cereals such as barley etc.). The protein is of value as a feed ingredient, but can be contaminated with copper as many distillation process are undertaken within copper (Cu) vessels and this can lead to the acidic waste (by-product) being rich in copper salts or complexes.

To be used in fish feed as a direct fishmeal replacer, it would be commercially advantageous if the by-products have protein concentrations at least similar to fishmeal (i.e. greater than 65%). The currently available by-products do not meet this criterion with maximum protein levels around 35%. Fish have very specific nutrient requirements, including essential amino acids. The amino acid requirements of the main fish species farmed in Europe and that in commercially available distillery by-products is summarised below. Lysine levels (often the first limiting amino acids in feed diets) in distillery by-products are less than fish requirements, except in the case of dark grains and pot ale syrup (spey syrup) from malt distilleries. In all cases, the methionine levels are less than required, although this is typical of plant protein sources. Pot ale thus is one of the few distillery by-products with the correct amino acid profile suitable for fish, in particular salmon feed. However, increased protein concentration and reduced carbohydrate and phytate levels would be required to make it more compatible with fish feed.

TABLE 3

The amino acid requirements of important European aquaculture species (as % minimum of dietary protein) and amino acid composition of fish meal

| Amino acid | Atlantic Salmon | Rainbow Trout | European seabass | Fishmeal |
| --- | --- | --- | --- | --- |
| Arginine | 3.7 | 4.7 | 4.6 | 5.8 |
| Histidine | 1.8 | 1.6 | 1.6 | 2.2 |
| Isoleucine | 1.8 | 1.9 | 2.6 | 4.3 |
| Leucine | 3.2 | 3.3 | 4.3 | 7.0 |
| Lysine | 4.1 | 4.2 | 4.8 | 7.5 |
| Methionine | 2.3 | 2.3 | 2.3 | 2.8 |
| Phenylalanine | 2.8 | 2.8 | 2.6 | 3.8 |
| Threonine | 0.5 | 1.9 | 2.7 | 4.1 |
| Tryptophan | 0.5 | 0.5 | 0.6 | 1.1 |
| Valine | 3.0 | 3.0 | 2.9 | 4.9 |

TABLE 4

Composition of commercially available by-products from distilleries

| Product | Draff | Dark grains | EU DDGS | US DDGS | Spey syrup | Proflo syrup |
| --- | --- | --- | --- | --- | --- | --- |
| DM (%) | 20-24 | 90 | 90 | 89 | 42 | 24 |
| CP | 22-24 | 24 | 29 | 30 | 32 | 35 |
| Oil | 9 | 9 | 10 | 11 | 1.0 | 4.5 |
| NDF[b] | 62 | 41 | 36 | 34 | 1.0 | 10 |
| Starch | 1.7 | 4.0 | 1.0 | 9.3 | 1.0 | 2.0 |
| Sugar | 2.0 | 2.0 | 1.0 | 1.7 | 2.0 | 5.0 |
| Lysine | 3.9 | 4.5 | 2.7 | 3.0 | 6.5 | 3.2 |
| Methionine | 1.5 | 1.8 | 1.9 | 2.0 | 1.1 | 1.5 |
| Cysteine | 2.1 | 2.1 | 1.5 | 2.0 | 2.1 | 1.5 |
| Histidine | 2.1 | 2.6 | 2.6 | 2.7 | 3.2 | 3.2 |
| Threonine | 3.8 | 4.5 | 3.7 | 3.7 | 5.6 | 3.2 |

The components are expressed as dry matter (M) with amino acids as % crude protein (CP). The data for draft and dark grains (distillers barley pellets) from Scottish malt distilleries, EU DDGS (imported corn distillers from outside UK), spey syrup (pot ale syrup from Scotch malt distilleries) and Proflo syrup (syrup from Vivergo wheat bioethanol plant in Yorkshire, England) NDF refers to neutral detergent fibre, roughly equivalent to hemicellulose, true cellulose and lignin.

In an example, the pot ale water based stream used in the process of the present invention includes dissolved solids and an insoluble solids fraction. In embodiments these two fractions can be separated into a clarified fraction and solids fraction, respectively with the desired proteins further separated from the clarified fraction of pot ale. The insoluble solids fraction of the pot ale mainly consists of yeast and yeast residues. The protein concentration in the clarified fraction can be improved by treating the insoluble solids fraction by known single or combined physicochemical and enzymatic processes to release protein components (lysis step). This optional lysis step allows the nutritive value of the protein product to be controlled.

In embodiments, the soluble proteins were selectively separated by preferentially binding these proteins in the clarified pot ale to an adsorbent. This enabled the potential anti-nutritional compounds in pot ale such as Cu, fibre, phytate, polyphenols and carbohydrates to be separated from the protein product. The process offers considerable advantages over the standard evaporation method for preparing pot ale syrup as an animal feed in that it doesn't incur high energy costs. Additionally evaporation can suffer from high greenhouse gas emissions and the high temperatures used may have a deleterious effect on protein quality. Evaporation concentrates all the components in pot ale, including non-desirable compounds such as phytate and copper. The separation of the protein from the other distillation residues, offers the advantage that the protein can be used in a wide range of feed ingredients such as use in aquaculture and pet food. The method can also be used to selectively separate specific proteins or a mixture of proteins, which have surprising foaming properties and which have potential uses as functional proteins in human, animal, pet and fish food formulations.

FIG. 1 describes the recovery of proteins from a malt whisky by-product known as pot ale or burnt ale. In this embodiment, the first step (Stage 1) in the protein recovery process is the separation of the solid particles. Typically, disc stack centrifuges, scroll decanters or hydrocyclones can be used for this purpose, providing that at a centrifugal field of at least 4000 g is achieved in order to match the output of by-product generation and economical demands. A secondary solid removal step (Stage 2) may be included to ensure that minimal quantities of particles are introduced to the equipment involved in subsequent protein purification steps. A failure to achieve this might imply a serious reduction in process outputs. Typical equipment used for secondary filtration might include filter bags or filter cartridges with a maximum pore diameter of 5, suitably 4, 3, 2 or 1 µm. The insoluble solids containing stream from Stage 1 and 2 can be dried (Stage 3) into a yeast product. In Stage 4, the protein components can be selectively removed from the liquid by-product stream and concentrated. This involves a primary protein concentration process that can be achieved by a chromatography step. Types of chromatography that can be utilised include adsorption matrices with properties such as ion exchange (IEX), size exclusion, affinity or any other appropriate type used in liquid chromatography systems. After the primary protein concentration step, a further step might be necessary in order to increase concentration and the purity of a particular protein or proteins of interest. For this step an additional chromatographic step may be included (Stage 5). An ultrafiltration/diafiltration or evaporation step can be used (Stage 6) to concentrate the protein mixture further after the chromatography steps. The type of filter for ultrafiltration/diafiltration will depend on the physical and chemical properties of the desired protein or proteins. A suitable filter material will then have for example, hydrophilic or hydrophobic properties and a nominal molecular weight cut off between 3-1000 kDa. A final step in the overall process includes further concentration, specifically removal of water (Stage 7). Typical moisture content of protein powders are less than 20%. For this purpose, driers might be used that might include: cross-circulation and through-circulation driers, tray driers, tunnel driers, rotary driers, drum driers, spray driers and/or freeze drier. The drying stages (3 and 7) can be combined as one stage to provide a high-protein yeast dry product consisting of the solids removed during steps 1 and 2 and the proteins separated by chromatography. The protein depleted waste stream and the streams resulting from equilibration and regeneration of the adsorption matrix during Stage 4-5 and waste streams from Stage 6 can enter waste water treatment systems (7). These streams are particularly suited to anaerobic digestion systems. In this case, the gas generated can be used as an energy source in other steps in the process, providing a truly integrated, low energy and environmentally sustainable process.

Example 1: Components of Interest in Pot Ale and Corresponding Clarified and Insoluble Fractions The typical analysis of pot ale from a Scottish malt whisky distillery is shown in Table 5 and Table 6. Up to 6 different independent batches of pot ale were analysed and the mean data are shown. Pot ale was analysed as either a total fraction (termed total pot ale) or separated into pellet (solid fraction) and supernatant (clarified fraction) by centrifugation. These correspond to the fractions entering stage 1, 2 and 4 respectively, as outlined in FIG. 1. Dry matter (DM) content of samples was determined by drying representative samples at 105° C. for 24 hours. Total polyphenols in the clarified fraction was analysed according to the ASBC Method Beer-35 for total Polyphenol analysis of beer (ASBC 1992) and total carbohydrates in this fraction was determined using the phenol-sulphuric acid assay according to Fournier (2001). Flame Atomic Absorption Spectroscopy was used to analyse the concentration of the macroelements Ca, Na, Mg and K and microelements Cu, Fe, Mn and Zn. Elements in the clarified fractions were analysed directly with reference to the relevant standards. For the total pot ale, samples were digested with 6 M $HNO_3$ prior to analysis. The concentration of elements in the solids fraction was determined as the difference between the other two fractions. Free and available phosphorous and corresponding phytate content of the total pot ale and clarified fraction was analysed using a Megazyme Phytic acid (Phytate)/Total phosphorous Kit (K-PHYT). The solids fraction was determined as the difference between the total and dissolved fractions. For nitrogen and amino acid analysis, samples were freeze-dried to less than 15% moisture. Both total aliquots and solid fractions were freeze-dried. It was not possible to freeze dry clarified fractions and only the total and solid fractions were analysed and the clarified fraction composition determined as the difference between these two samples. Nitrogen was analysed using an Exeter Analytical CE440 Elemental Analyser and the crude protein content was estimated as N×6.25. Amino acid analysis was by acid hydrolysis followed by ion exchange chromatography with ninhydrin detection and was conducted by Abingdon Health Laboratory Services at the University of Birmingham. The content of specific amino acids was calculated as a % of the crude protein as determined by CHN analysis. For this method, asparagine and glutamine are completely converted to aspartic acid and glutamic acid, respectively.

Comprehensive analysis of pot ale including differences between clarified and solid fractions is not readily available. What is interesting from this data is that approximately two thirds of the protein in pot ale is in the clarified fraction. The concentration of soluble protein can be further increased by lysing the yeast cells. This fraction also contains 1% polyphenol, 43% carbohydrate and % phytate with over 1.6% phosphorous on a dry matter basis. These components are undesirable in certain feed applications, particularly in aquafeed and, without further processing, the degree of incorporation of clarified pot ale in feeds would be restricted to a low level.

Example 2: Analysis of Proteins in Pot Ale by SDS-PAGE

The proteins in the clarified fraction were further analysed by SDS-PAGE analysis. Firstly, samples were concentrated and dialysed using Amicon Ultra-15 3K Centrifugal Filter Tubes (Merck Millipore Ltd., Cork, Ireland). The protein concentration was determined by Bradford assay (Bradford 1976) and samples analysed by SDS-PAGE. Samples of known protein concentration were mixed with equal volumes of Laemmli sample buffer (Sigma-Aldrich Ltd., Dorset, England), heated at 70° C. for 10 min, cooled on ice and loaded on to 4-20% precast polyacrylamide gels (Bio-Rad Mini-Protean TGX precast gels, Bio-Rad Laboratories, Herts, UK). Gels were run using a Bio-Rad Mini-Protean Tetra Cell System for mini precast gels with Tris-Glycine running buffer. A prestained, broad range (7-175 kDa) protein marker (New England Biolabs (UK) Ltd., Herts, UK) was run with all gels to estimate protein molecular weight. Electrophoresis was at 180 V for approximately 40 min and stopped when the dye front reached the bottom of the gel. After electrophoresis, gels were rinsed with water and stained overnight with a Colloidal Coomassie Blue stain. Gels were rinsed and destained with water until the background stain was removed. The SDS-PAGE gels were scanned with a VersaDoc imaging system (Bio-Rad) and images were analysed using Bio-Rad's Image Lab software to estimate the molecular weight of protein bands.

Figure 3:
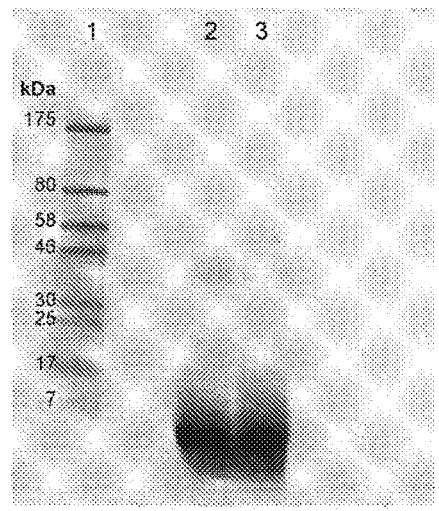

Typically, the clarified fraction showed two protein bands of different molecular weight ranges when analysed by SDS-PAGE—a broad band at approximately 7-15 kDa and a higher molecular weight band at 38-42 kDa (FIG. 3). The two bands are within the size range of LTP1 and Protein Z, which originate from barley (Leiper et al., 2003 [Leiper, K. A., Stewart, G. G., McKeown, I. P. 2003. Beer polypeptides and silica gel. Part II. Polypeptides involved in form formation. Journal of the Institute of Brewing. 109:73-79.]). It should be highlighted however that the molecular weights reported here are only approximations as a prestained protein marker was used. The bands also appear quite 'fuzzy' which is typical for proteins that have glycated amino acid residues. Further analysis has shown that the lower molecular weight band is composed of components of different apparent molecular weights. This can be attributed to either the LTP1 protein being glycated to different degrees or hordein fragments from the barley also being present in the pot ale.

This is the first time that the proteins in pot ale have been tentatively identified. What is surprising is that the protein profile by SDS-PAGE is similar to that of beer (Leiper 2003), despite the different processing steps involved. During whisky production, proteins are continuously modified during the fermentation by proteolytic enzymes and it would not be unreasonable to expect that the excessive heating during distillation would lead to further protein precipitation and proteolysis. Based on this it is surprising that proteins greater than 5 kDa are still present in the clarified pot ale.

TABLE 5

Analysis of total pot ale and clarified and solid fractions. All concentrations are on a dry matter basis unless stated otherwise.

| Component | Total Pot Ale | Clarified fraction | Solids fraction |
|---|---|---|---|
| pH | 3.9 | N/A | N/A |
| Dry matter (%) | 5.1 | 3.8 | 1.2 |
| Protein (%) | 32.3 | 27.9 | 53.0 |
| Total carbohydrate (%) | N/A | 43.4 | N/A |
| Polyphenol (g/kg) | N/A | 11.6 | N/A |
| P (available) (g/kg) | 10.4 | 13.4 | 2.9 |
| P (total) (g/kg) | 13.7 | 16.3 | 6.2 |
| Phytate (g/kg) | 11.5 | 10.8 | 13.6 |
| Ca (g/kg) | 1.3 | 1.0 | 2.5 |
| Mg (g/kg) | 6.2 | 6.6 | 6.5 |
| K (g/kg) | 23.1 | 25.5 | 20.4 |
| Na (g/kg) | 0.7 | 0.7 | 0.9 |
| Cu (mg/kg) | 57 | 18.1 | 197.9 |
| Fe (mg/kg) | 37.0 | 7.1 | 96.8 |
| Mn (mg/kg) | 13.6 | 11.3 | 23.7 |
| Zn (mg/kg) | 24.6 | 18.1 | 48.4 |

TABLE 6

Analysis of some of the amino acids in the protein of pot ale and clarified and solid fractions. Amino acids are shown as % crude protein based on N analysis.

| Amino acid (mol %) | Total Pot Ale | Clarified fraction | Solids fraction |
|---|---|---|---|
| Alanine | 3.6 | 2.8 | 4.7 |
| Arginine | 2.3 | 0.9 | 4.1 |
| Aspartic acid | 6.1 | 4.3 | 8.5 |
| Glutamic acid | 7.3 | 4.8 | 10.5 |
| Glycine | 3.2 | 3.2 | 3.3 |
| Histidine | 3.5 | 4.0 | 2.7 |
| Isoleucine | 2.8 | 1.5 | 4.5 |
| Leucine | 4.2 | 2.0 | 7.1 |
| Lysine | 4.1 | 2.5 | 6.4 |
| Methionine | 0.9 | 0.4 | 1.6 |
| Phenylalanine | 2.4 | 0.9 | 4.5 |
| Proline | 7.3 | 10.2 | 3.4 |
| Serine | 3.1 | 1.8 | 4.7 |
| Threonine | 3.1 | 1.9 | 4.6 |
| Tyrosine | 1.5 | 0.6 | 2.7 |
| Valine | 3.5 | 2.2 | 5.1 |

Example 3: Separation and Recovery of Pot Ale Proteins Using Capto S

Figure 4:
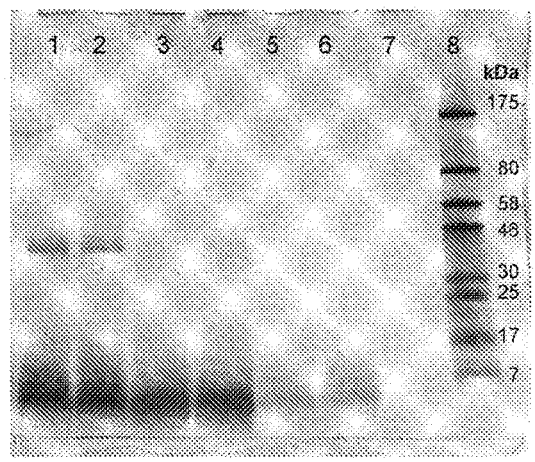

The proteins in the dissolved solids fraction were separated and recovered by chromatography using the resin Capto S, a strong cation exchange medium supplied in a prepacked column (GE Healthcare). Three protein fractions were collected sequentially after elution with 0.1 M sodium acetate at pH 4.5 containing increasing amounts of NaCl at 0.2, 0.4 and 0.6 M. This allowed differential separation of pot ale proteins as demonstrated by SDS-PAGE analysis (FIG. 4).

Example 4: Solid Phase (Matrix) Conditioning

Figure 2:
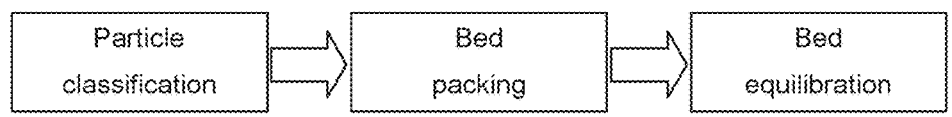

A solid phase, matrix, adsorbent or resin was conditioned prior to being introduced into the column to give maximum (protein) adsorption capacity and processing flow rates while maintaining a low pressure drop across the column. In this example, zeolite clinoptilolite also known as "zeolite c" was used in a 5 cm diameter column. Based on the inventor's calculations, columns up to 1 m³ are considered to be possible and will be operable under the desired pressure and flow conditions Three sequential steps (FIG. 2) were used in order to achieve the objectives mentioned above (maximum adsorption, maximum flowrate and minimum pressure). The "Partide classification" step aims to remove small size particles (suitably less than 90 micrometers diameter). To achieve this, a suitably less than 90 micron sieve was used and then subsequently, the particles were introduced into the column and water was pumped from the bottom of the column and the top of the column was left open causing the smaller particles to float (bed fluidisation) and then to leave the column. This process is also known as elutriation. In this example a 5 cm diameter column with typical flow rates up to 80 ml/min was used. To ensure that all the small particles were removed, this process was carried out for at least 1 hour.

The second step "Bed packing" maximises the quantity of the solid phase per unit of volume. To achieve this, water was pumped through the column from the top to the bottom. For the 5 cm diameter column, flowrates were typically in the order of 100-150 ml/min for at least 2 hours. During this time it is important to ensure no air is trapped in the column and that the column is not over pressuring.

The final step, "Bed equilibration" is used to remove contaminants attached to the resin and to charge the resin particles appropriately in order to ensure maximum protein-adsorbent interaction. In this case, a solution of 1 M NaOH was used at a flowrate of approximately 40 ml/min (downwards flow) for at least 1 hour.

Subsequently, distilled, deionised water was used to remove any salts at a flowrate of approximately 40 ml/min for at least 1 hour. Finally a buffer solution with a pH range between 3-5, e.g. acetate buffer, was used to ensure that solid particles were charged in order to ensure maximum attachment of proteins or any other substance of interest to the solid phase. This step normally is carried out at flowrates up to 40 ml/min for at least one hour.

Example 5: Separation and Recovery of Pot Ale Proteins Using Food-Grade Zeolite

Ion exchange chromatography processes using columns packed with zeolite C and conditioned as described in Example 4 were used to separate and recover pot ale proteins. The clarified fraction of pot ale typically contained 0.7 g/L protein as determined by Bradford assay (Bradford, 1976) and was loaded at rate of 0.1 to 2 column volumes (CV) per minute. Following the loading step a washing step with 0.2 M acetate buffer, pH 3.5 was used to remove all particles that did not bind to the solid phase of the matrix and to remove unwanted components or contaminants. After the washing step, an elution step was followed. Alkali buffers such as a carbonate or phosphate buffer with a buffering capacity 7-11 pH units might be used at similar flow rates used previously. A series of solutions of different pH can be used in order to selectively detach the proteins adsorbed to the solid phase of the column.

Figure 5:
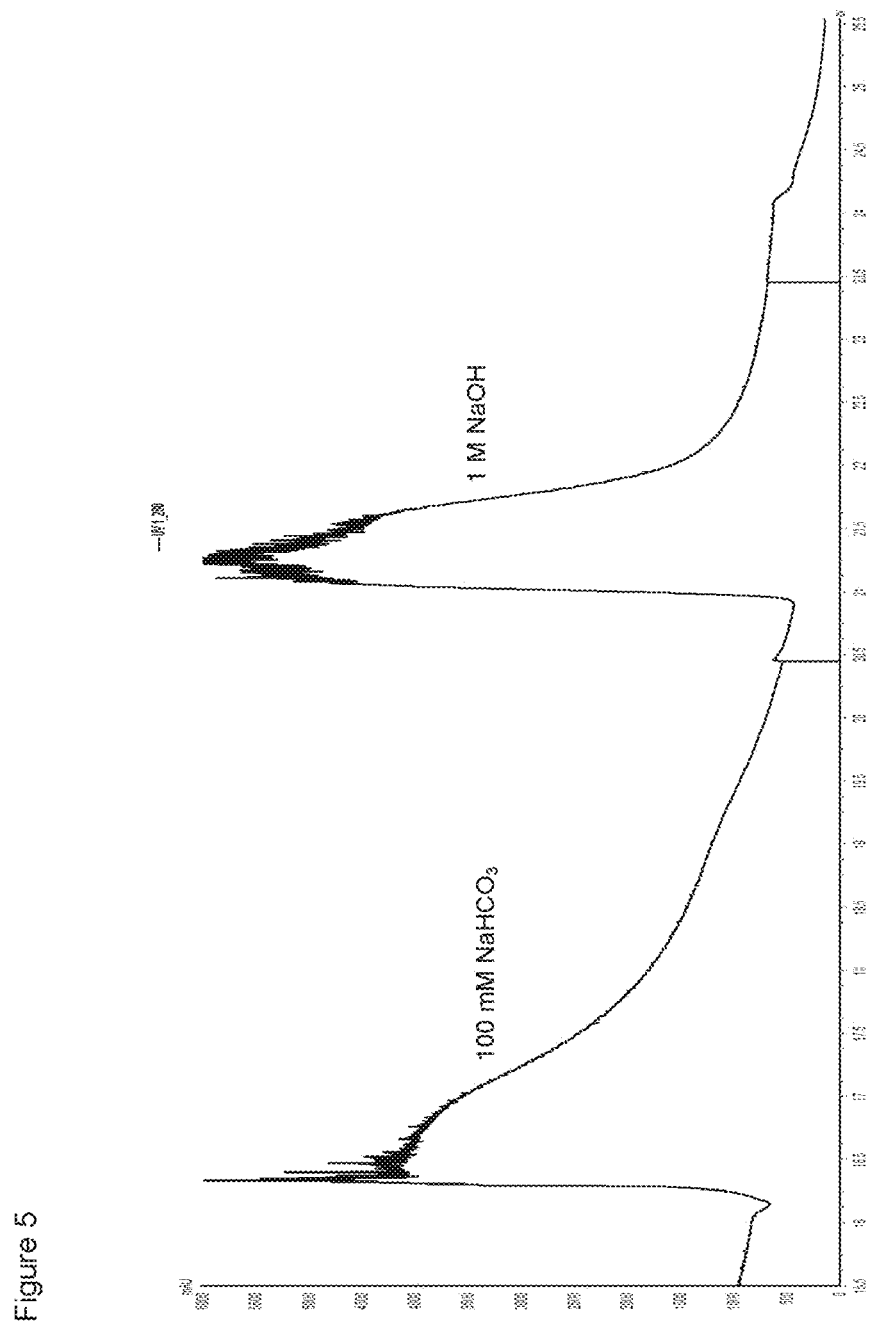
FIG. 5 shows the protein elution from zeolite c using 100 mM $NaHCO_3$ followed by 1 M NaOH. Chromatograms were generated by the AKTA Avant and show time from initial chromatography set-up on the x-axis and protein concentration as indicated by Absorbance at 280 nm on the y-axis.
Figure 6:
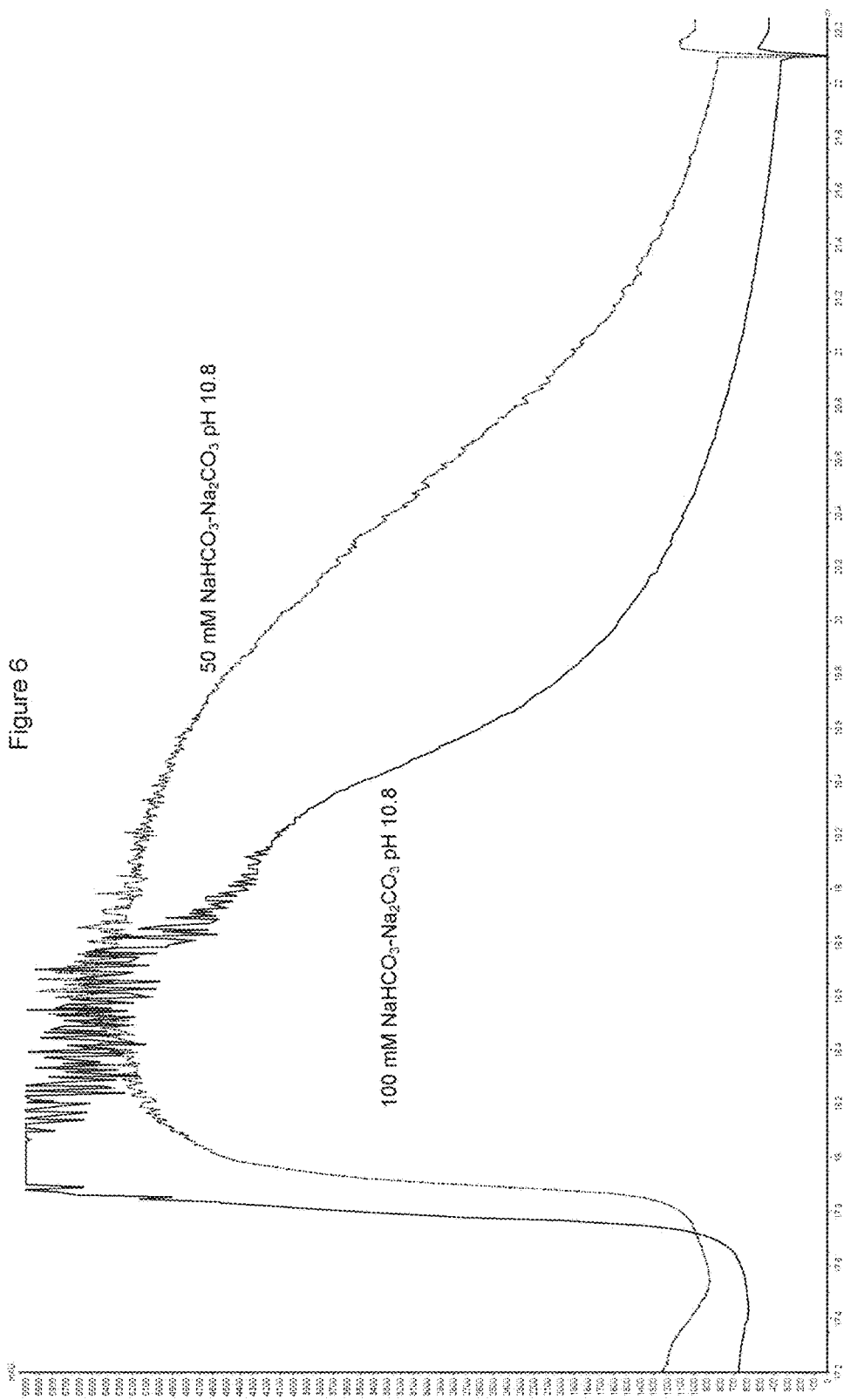
FIG. 6 shows the protein elution from zeolite c using either 50 or 100 mM $NaHCO_3$—$Na_2CO_3$ buffer at pH 10.8. Chromatograms were generated by the AKTA Avant and show time from initial chromatography set-up on the x-axis and protein concentration as indicated by Absorbance at 280 nm on the y-axis.
Figure 7:
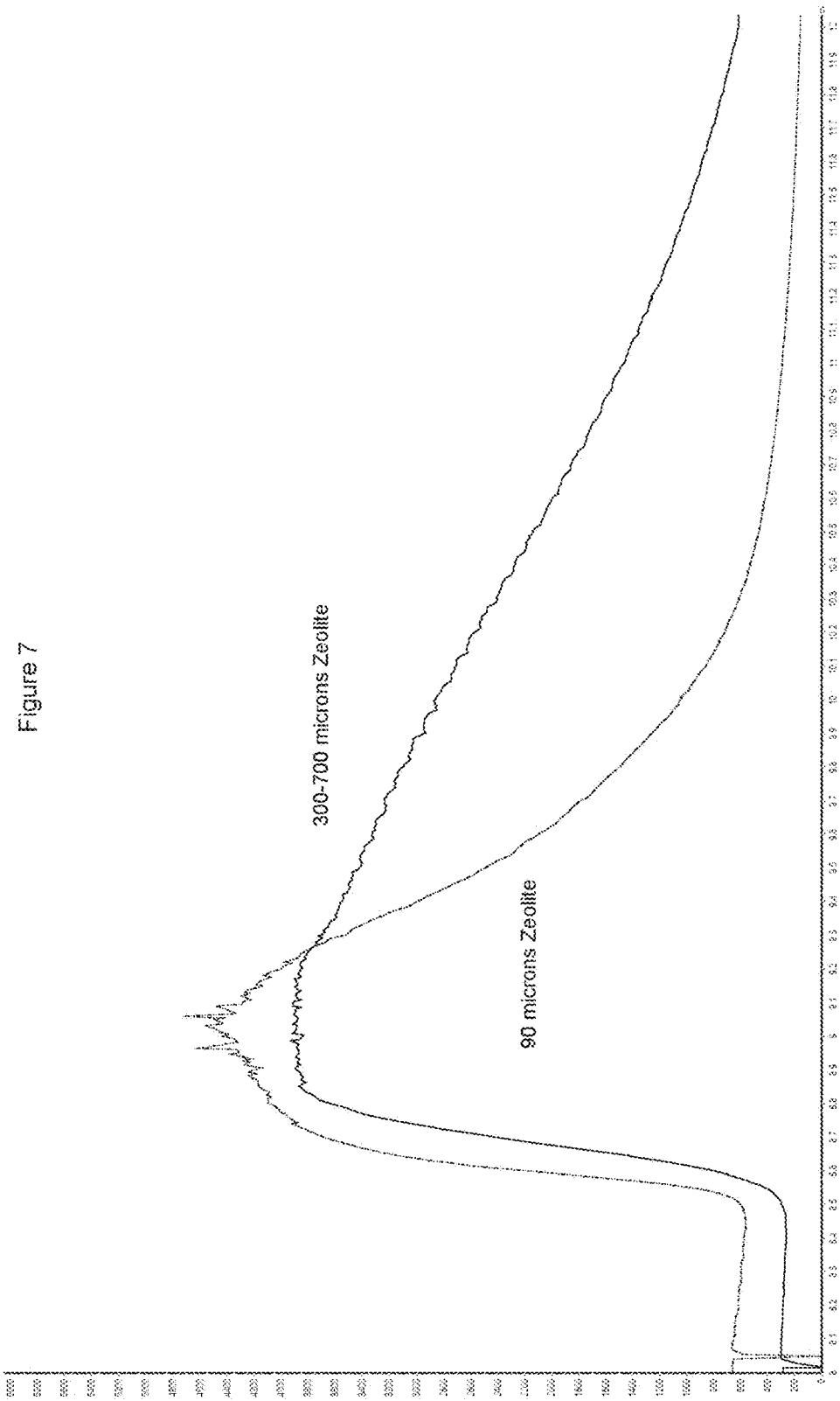
FIG. 7 shows the protein elution from either fine or coarse grade zeolite c, using 100 mM NaHCO$_3$—Na$_2$CO$_3$ buffer at pH 10.8. Chromatograms were generated by the AKTA Avant and show time from initial chromatography set-up on the x-axis and protein concentration as indicated by Absorbance at 280 nm on the y-axis.
Figure 8:
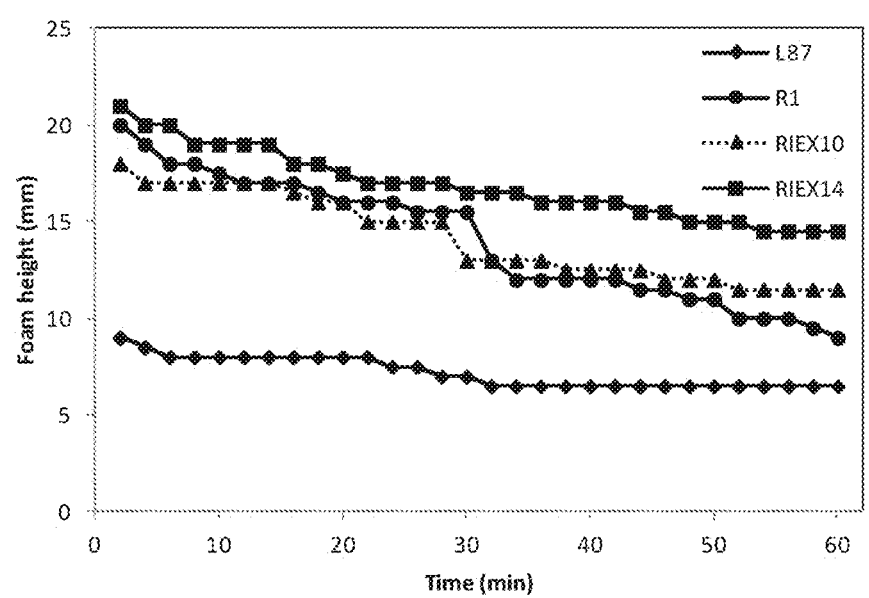
FIG. 8 is a plot comparing the stability of foams produced by the proteins in pot ale concentrated by ultrafiltration and dialysed in water (R1), proteins in pot ale separated by chromatography using zeolite C and eluted as described in Example 4 (RIEX10), pot ale proteins recovered from zeolite C by elution with 1 M NaOH (RIEX14) and lacprodan DI 7017, a commercial available dairy protein (L87).

A number of experiments were ran to test elution under different conditions and also to test the use of two different size grades of zeolite C. Chromatograms showing elution of proteins as indicated by absorbance at 280 nm as generated by the AKTA Avant (GE Healthcare) under different elution conditions are shown in FIGS. 5-7. Time from initial chromatography set-up is shown on the x-axis with absorbance at 280 nm on the y-axis. Pot ale was loaded on to zeolite columns under similar conditions. Fine grade zeolite was used in all examples except for FIG. 7 where coarse and fine grade zeolite were compared. Typical chromatograms for elution using 100 mM NaHCO$_3$ followed by 1 M NaOH (FIG. 5), 50 or 100 mM NaHCO$_3$—Na$_2$CO$_3$, pH 10.8 buffer (FIG. 6) and elution using 100 mM NaHCO$_3$—Na$_2$CO$_3$, pH 10.8 buffer from fine or coarse zeolite (FIG. 7) are provided. Sizes of less than 40 microns are generally not suitable. Two different size ranges of clinoptilolite were tested; 90 and 300-700 microns. Whilst the elution profiles were different, this was likely related to different flow conditions in the matrix. Both size ranges showed similar capacity for protein binding and were both suitable for preparing a protein product from pot ale.

For the example using 0.1 M NaHCO$_3$ at pH 8 for elution and 2 L of eluent with a Bradford protein content of 1.3 g/L was retained for analysis. Following the elution step, a high pH (pH 13-14) solution was added to the column and further proteins detached from the solid phase of the column. A NaOH solution (less than 10%) can be used at similar flow rates described earlier for at least 13 Column Volumes. Collection of proteins from this step is optional, but the introduction of this step is important in order to sanitise the adsorbent materials and ensure contaminants such as toxins or microorganism are removed from the system. Additionally, a 20% ethanol solution can be used to improve sanitisation and decontamination. The column can then be regenerated by flushing with water followed by low pH buffers (pH 3-5) such as acetate and citrate buffers prior to being reused.

Example 6—Analysis of Collected Fraction of First Elution Step at pH 8

The fraction collected at pH 8 was analysed for protein, and carbohydrate content. The product was 50% crude protein with less than 0.5% carbohydrate. The amino acid composition of this fraction is detailed in Table 7. Tryptophan usually suffers complete loss during hydrolysis and was analysed separately. Cysteic acid was analysed separately and expressed as cystine. This confirmed that zeolite resins are suitable for preferentially separating the proteins from other dissolved components which may be non-desirable in feed ingredients.

TABLE 7

Amino acid composition (as % crude protein, CP) of a separated pot ale sample prepared using zeolite C

| Amino acid (% CP) | Separated pot ale |
| --- | --- |
| Alanine | 2.8 |
| Arginine | 3.9 |
| Aspartic acid | 6.5 |
| Cystine | 15.4 |
| Glutamic acid | 12.9 |
| Glycine | 4.5 |
| Histidine | 3.2 |
| Isoleucine | 2.3 |
| Leucine | 4.2 |
| Lysine | 3.4 |
| Methionine | 1.2 |
| Phenylalanine | 2.1 |
| Proline | 5.8 |
| Serine | 3.4 |
| Threonine | 3.1 |
| Tryptophan | 3.9 |
| Tyrosine | 2.7 |
| Valine | 3.5 |

Example 7: Foam Potential Properties of Pot Ale Proteins

The ability of pot ale proteins to form foam and the stability of this foam was compared to known foam-active protein ingredients.

The foaming ability and stability of pot ale proteins were compared to that of lacprodan (L7017 from Aria Foods). Three different samples of pot ale proteins were prepared. R1 was a 3 KDa ultrafiltration preparation prepared as follows: The dissolved solids fraction of pot ale was centrifuged in an Amicon 3 KDa separator tube and the retained protein resuspended in water and centrifuged again. The protein content of the retentate was analysed and the protein diluted in buffer. RIEX10 and RIEX14 were obtained by chromatographic separation using zeolite C with 10 and 14 referring to the protein fraction recovered after elution with carbonate buffer at pH 10 (as described in Example 4) and 1 M NaOH respectively. The protein in these samples was further concentrated using 3 KDa Amicon tubes as above and dialysed with water.

The protein concentration of the samples was determined by Bradford assay and samples were diluted in 10 mM potassium phosphate, 35 mM NaCl, pH 7.0 buffer to give a concentration of 0.01 g/l protein.

The ability to form foam and the stability of this was assayed by adding 10 ml of protein solution to a 50 ml centrifuge tube and whipping with an Aerolatte frother for 1 min. The height of the foam was measured 2 min after the start of whipping and monitored at 2 min intervals for 60 min.

All documents referred to in this specification are herein incorporated by reference. Various modifications and variations to the described embodiments of the inventions will be apparent to those skilled in the art without departing from the scope of the invention. Although the invention has been described in connection with specific preferred embodiments, it should be understood that the invention as claimed should not be unduly limited to such specific embodiments. Indeed various modifications of the described modes of carrying out the invention which are obvious to those skilled in the art are intended to be covered by the present invention.

The invention claimed is:

1. A process for the recovery of proteinaceous matter, from a by-product stream arising from distillation processes, the process comprising:
   optionally, lysing or disrupting cells present in the by-product stream;
   removing solid matter from the by-product stream to yield a clarified proteinaceous matter containing solution;
   contacting the clarified proteinaceous matter containing solution with an adsorption matrix under conditions such that the proteinaceous matter binds to the matrix; wherein the adsorption matrix comprises a silica content of greater than 50% wt; and
   altering the conditions to cause release of all of or a specific fraction of the proteinaceous matter bound to the adsorption matrix.

2. The process of claim 1, wherein the step of removing solid matter from the by-product stream utilises a two stage process.

3. The process of claim 1, wherein the by-product stream is selected from pot ale, spent wash, spent lees, stillage, draff, spent grain, hot (trub) or cold break from an alcohol or biofuel distillation process, or a combination of at least two by-product streams.

4. The process of claim 1, wherein the by-product is selected from pot ale.

5. The process of claim 1, wherein the by-product stream has a pH range of between 2 to 6 when the proteinaceous matter in the by-product stream binds to the adsorption matrix.

6. The process of claim 1, wherein the adsorption matrix has a silica content of greater than 70% wt.

7. The process of claim 1, wherein the adsorption matrix comprises an aluminosilicate.

8. The process of claim 1, wherein the adsorption matrix comprises a clay mineral.

9. The process of claim 1, wherein the adsorption matrix comprises any one of the following: diatomaceous earth, bentonite, kieselguhrs, and/or zeolites.

10. The process of claim 9, wherein the adsorption matrix is zeolite clinoptilolite.

11. The process of claim 1, wherein the step of altering the conditions to cause release of all of or a specific fraction of the proteinaceous matter bound to the adsorption matrix comprises elution with a phosphate or carbonate buffer in the pH range 7-11; or sodium hydroxide in the pH range 10-14.

* * * * *

SEQUENCE LISTING

```
<160> NUMBER OF SEQ ID NOS: 3

<210> SEQ ID NO 1
<211> LENGTH: 399
<212> TYPE: PRT
<213> ORGANISM: Hordeum vulgare

<400> SEQUENCE: 1

Met Ala Thr Thr Leu Ala Thr Asp Val Arg Leu Ser Ile Ala His Gln
1               5                   10                  15

Thr Arg Phe Ala Leu Arg Leu Arg Ser Ala Ile Ser Ser Asn Pro Glu
            20                  25                  30

Arg Ala Ala Gly Asn Val Ala Phe Ser Pro Leu Ser Leu His Val Ala
        35                  40                  45

Leu Ser Leu Ile Thr Ala Gly Ala Ala Thr Arg Asp Gln Leu Val
    50                  55                  60

Ala Ile Leu Gly Asp Gly Ala Gly Asp Ala Lys Glu Leu Asn Ala
65                  70                  75                  80

Leu Ala Glu Gln Val Val Gln Phe Val Leu Ala Asn Glu Ser Ser Thr
                85                  90                  95

Gly Gly Pro Arg Ile Ala Phe Ala Asn Gly Ile Phe Val Asp Ala Ser
            100                 105                 110

Leu Ser Leu Lys Pro Ser Phe Glu Glu Leu Ala Val Cys Gln Tyr Lys
        115                 120                 125

Ala Lys Thr Gln Ser Val Asp Phe Gln His Lys Thr Leu Glu Ala Val
    130                 135                 140

Gly Gln Val Asn Ser Trp Val Glu Gln Val Thr Thr Gly Leu Ile Lys
145                 150                 155                 160

Gln Ile Leu Pro Pro Gly Ser Val Asp Asn Thr Thr Lys Leu Ile Leu
                165                 170                 175

Gly Asn Ala Leu Tyr Phe Lys Gly Ala Trp Asp Gln Lys Phe Asp Glu
            180                 185                 190

Ser Asn Thr Lys Cys Asp Ser Phe His Leu Leu Asp Gly Ser Ser Ile
        195                 200                 205

Gln Thr Gln Phe Met Ser Ser Thr Lys Lys Gln Tyr Ile Ser Ser Ser
    210                 215                 220

Asp Asn Leu Lys Val Leu Lys Leu Pro Tyr Ala Lys Gly His Asp Lys
225                 230                 235                 240

Arg Gln Phe Ser Met Tyr Ile Leu Leu Pro Gly Ala Gln Asp Gly Leu
                245                 250                 255

Trp Ser Leu Ala Lys Arg Leu Ser Thr Glu Pro Glu Phe Ile Glu Asn
            260                 265                 270

His Ile Pro Lys Gln Thr Val Glu Val Gly Arg Phe Gln Leu Pro Lys
        275                 280                 285

Phe Lys Ile Ser Tyr Gln Phe Glu Ala Ser Ser Leu Leu Arg Ala Leu
    290                 295                 300
```

-continued

Gly Leu Gln Leu Pro Phe Ser Glu Glu Ala Asp Leu Ser Glu Met Val
305                 310                 315                 320

Asp Ser Ser Gln Gly Leu Glu Ile Ser His Val Phe His Lys Ser Phe
            325                 330                 335

Val Glu Val Asn Glu Glu Gly Thr Glu Ala Gly Ala Ala Thr Val Ala
            340                 345                 350

Met Gly Val Ala Met Ser Met Pro Leu Lys Val Asp Leu Val Asp Phe
            355                 360                 365

Val Ala Asn His Pro Phe Leu Phe Leu Ile Arg Glu Asp Ile Ala Gly
            370                 375                 380

Val Val Val Phe Val Gly His Val Thr Asn Pro Leu Ile Ser Ala
385                 390                 395

<210> SEQ ID NO 2
<211> LENGTH: 397
<212> TYPE: PRT
<213> ORGANISM: Hordeum vulgare

<400> SEQUENCE: 2

Met Ala Thr Thr Leu Thr Thr Asp Leu Arg Leu Ser Ile Ala His Gln
1               5                   10                  15

Thr Arg Phe Gly Leu Arg Leu Ala Ser Ala Ile Ser Ser Asp Pro Glu
            20                  25                  30

Ser Ala Ala Thr Asn Val Ala Phe Ser Pro Val Ser Leu His Val Ala
            35                  40                  45

Leu Ser Leu Val Ala Ala Gly Ala Arg Gly Ala Thr Arg Asp Gln Leu
        50                  55                  60

Val Ala Val Leu Gly Gly Gly Ala Gly Glu Ala Glu Ala Leu Gln
65                  70                  75                  80

Ser Leu Ala Glu Gln Val Val Gln Phe Val Leu Ala Asp Ala Ser Ile
                85                  90                  95

Asn Ser Gly Pro Arg Ile Ala Phe Ala Asn Gly Val Phe Val Asp Ala
            100                 105                 110

Ser Leu Ser Leu Lys Pro Ser Phe Gln Glu Leu Ala Val Cys Asn Tyr
            115                 120                 125

Lys Ser Glu Val Gln Ser Val Asp Phe Lys Thr Lys Ala Pro Glu Ala
130                 135                 140

Ala Ser Gln Val Asn Ser Trp Val Lys Asn Val Thr Ala Gly Leu Ile
145                 150                 155                 160

Glu Glu Ile Leu Pro Ala Gly Ser Ile Asp Asn Thr Thr Arg Leu Val
                165                 170                 175

Leu Gly Asn Ala Leu Tyr Phe Lys Gly Leu Trp Thr Lys Lys Phe Asp
            180                 185                 190

Glu Ser Lys Thr Lys Tyr Asp Asp Phe His Leu Leu Asn Gly Ser Thr
            195                 200                 205

Val Gln Thr Pro Phe Met Ser Ser Thr Asn Lys Gln Tyr Leu Ser Ser
            210                 215                 220

Ser Asp Gly Leu Lys Val Leu Lys Leu Pro Tyr Gln His Gly Gly Asp
225                 230                 235                 240

Asn Arg Gln Phe Ser Met Tyr Ile Leu Leu Pro Glu Ala His Asp Gly
                245                 250                 255

Leu Ser Arg Leu Ala Gln Lys Leu Ser Thr Glu Pro Asp Phe Leu Glu
            260                 265                 270

Asn Arg Ile Pro Thr Glu Glu Val Glu Val Gly Gln Phe Met Leu Pro
            275                 280                 285

-continued

```
Lys Phe Lys Ile Ser Phe Gly Phe Glu Ala Asn Lys Leu Leu Lys Thr
            290                 295                 300

Leu Gly Leu Gln Leu Pro Phe Ser Leu Glu Ala Asn Leu Ser Glu Met
305                 310                 315                 320

Val Asn Ser Pro Met Gly Leu Tyr Ile Ser Ser Val Phe His Lys Thr
                325                 330                 335

Phe Val Glu Val Asp Glu Glu Gly Thr Lys Ala Gly Ala Ala Thr Gly
                340                 345                 350

Asp Val Ile Val Asp Arg Ser Leu Pro Ile Arg Met Asp Phe Val Ala
            355                 360                 365

Asn His Pro Phe Leu Phe Leu Ile Arg Glu Asp Ile Ala Gly Val Val
            370                 375                 380

Leu Phe Ile Gly His Val Ala Asn Pro Ala Val Ser Ser
385                 390                 395

<210> SEQ ID NO 3
<211> LENGTH: 117
<212> TYPE: PRT
<213> ORGANISM: Hordeum vulgare

<400> SEQUENCE: 3

Met Ala Arg Ala Gln Val Leu Leu Met Ala Ala Ala Leu Val Leu Met
1               5                   10                  15

Leu Thr Ala Ala Pro Arg Ala Ala Val Ala Leu Asn Cys Gly Gln Val
                20                  25                  30

Asp Ser Lys Met Lys Pro Cys Leu Thr Tyr Val Gln Gly Gly Pro Gly
            35                  40                  45

Pro Ser Gly Glu Cys Cys Asn Gly Val Arg Asp Leu His Asn Gln Ala
        50                  55                  60

Gln Ser Ser Gly Asp Arg Gln Thr Val Cys Asn Cys Leu Lys Gly Ile
65                  70                  75                  80

Ala Arg Gly Ile His Asn Leu Asn Leu Asn Asn Ala Ala Ser Ile Pro
                85                  90                  95

Ser Lys Cys Asn Val Asn Val Pro Tyr Thr Ile Ser Pro Asp Ile Asp
            100                 105                 110

Cys Ser Arg Ile Tyr
            115
```